United States Patent [19]

Reckel

[11] 4,046,871

[45] Sept. 6, 1977

[54] COMPOSITIONS AND SEROLOGICAL METHODS INCLUDING BOVINE SERUM ALBUMIN POLYMERS

[75] Inventor: Rudolph P. Reckel, Somerville, N.J.

[73] Assignee: Ortho Diagnostics Inc., Raritan, N.J.

[21] Appl. No.: 566,641

[22] Filed: Apr. 8, 1975

[51] Int. Cl.$^2$ .................. C07G 7/00; G01N 31/00; G01N 33/16
[52] U.S. Cl. ........................ 424/11; 260/112.5 R; 260/121; 424/8; 424/12; 424/13; 424/101; 424/177
[58] Field of Search ............ 424/8, 11, 12, 13, 88, 424/101, 177; 260/121, 112.5

[56] References Cited

U.S. PATENT DOCUMENTS

| | | | |
|---|---|---|---|
| 2,770,572 | 11/1956 | Eldon | 424/11 |
| 2,938,892 | 5/1960 | Sheehan | 260/121 X |

FOREIGN PATENT DOCUMENTS

| | | | |
|---|---|---|---|
| 1,257,263 | 12/1971 | United Kingdom | 424/12 |

OTHER PUBLICATIONS

Franz, Chem. Abs., vol. 77, 1972, Ab. No. 138309d.
Shrivastava, Chem. Ab. vol. 77, 1972, Ab. No. 71643n.
Westphal, Chem. Abs., vol. 79, 1973, Ab. No. 62698y.
Payne, Chem. Abs., vol. 80, 1974, Ab. No. 105502v.
Dunsford, Tech. in Blood Banking, Oliver & Boyd Pub., London, 1955, pp. 23-27.
Means, Chemical Modification of Proteins, Holden--Day, San Francisco, 1971, pp. 39-43, 145-148.
Goodfriend, Science, vol. 144, June 12, 1964, pp. 1344-1346.
Adler, The J. of Immunol., vol. 106, June, 1971, pp. 1684-1685.

*Primary Examiner*—Albert T. Meyers
*Assistant Examiner*—A. P. Fagelson
*Attorney, Agent, or Firm*—Alice O. Robertson

[57] ABSTRACT

New serological albumin compositions are provided which have greater potentiating capabilities than existing compositions in agglutination reactions of the IgG class of immune globulins. The essential component is at least one covalently bonded serum albumin polymer. The novel polymers are those containing from two to about eight or more monomeric albumin units which are joined to each other through a covalent peptide bond. Serological compositions may be prepared by polymerization of a dilute aqueous albumin solution, quenching of the reaction, precipitation of the products as solids, dissolution of albumin solids with or without separation of polymers in physiological or isotonic solutions. The compositions are useful as diluents for reagent preparation and for titration media, and as antibody detecting media.

10 Claims, No Drawings

COMPOSITIONS AND SEROLOGICAL METHODS INCLUDING BOVINE SERUM ALBUMIN POLYMERS

DESCRIPTION OF THE INVENTION

The present invention relates to novel serum albumin compositions, to their preparation and use, and to novel polymer components of such compositions.

In blood serology, the knowledge of the pressure of particular antibodies is very important. In blood transfusions, the knowledge of the presence of certain antibodies is essential. Presence of undetected antibodies may cause a transfusion reaction which may be fatal. Thus, when an antibody concentration is so low that they are absorbed by the cells instead of agglutinating it, it is often misinterpreted as compatibility when in fact it was a sensitizing injection. When a second transfusion is given a week to ten days later, a fatal reaction may occur. Even when the reaction is not fatal, it may reduce the normal life-span of transfused, incompatible cells necessitating subsequent transfusions. Such problems may be avoided by prior knowledge of all or most of the antibodies by the provision of a more sensitive antibody detection means.

Serum or plasma albumins have been used in blood group serology for about 30 years as a means to aid in the detection of some antibodies in blood serum which escape detection when the blood serum to be tested is contacted with a saline or isotonic solution of red blood cells. Agglutination of red cells by antibodies have been classified as (1) those occurring in low protein or low dielectric constant media such as isotonic salt solutions and (2) those occurring in high protein or high dielectric constant media. The antibodies reacting under the former conditions have been identified as belonging to the IgM class of immune globulins, while those reacting under the latter conditions have been identified as belonging to the IgG class. The theoretical explanation advanced for the ability of the protein to promote specific agglutination is that it raises the dielectric constant of the medium, thereby reducing the zeta potential of the cells and shortening the average intercellular distance to less than the distance necessary to be spanned by the IgG antibody molecules for agglutination. The protein employed in the detection medium is mammalian serum albumin, particularly bovine serum albumin, because of the availability of large quantities of beef blood. However, available bovine serum albumin solutions have been quite variable in their ability to raise the dielectric constant of water and therefore in their ability to promote the necessary agglutination in the detection of antibodies. The variability has not necessarily been avoided by employing higher concentrations of albumin. Moreover, available bovine serum albumin solutions are not of sufficient potentiating capability to avoid overlooking the existence of certain antibodies.

Attempts have been made heretofore to improve potentiating capabilities by modifying albumin compositions. However, modifications have not provided consistently superior compositions. Thus, Jones et al. (Nature, 224,519 (1969)) treated albumin with ethanol to obtain aggregates which were of apparent multiple molecular size of a natural albumin molecule. The alcohol treated albumin was reported to have higher potentiating capacity but probably because of the reversible nature of the aggregates resulting in difficult reproducibility of results, albumin compositions containing ethanol produced albumin aggregates have not gained acceptance as a potentiating medium. (Although the larger bodies were called "polymers" by Jones, and it is sometimes so called by others for convenience, it is generally recognized that they are aggregates and not true polymers because they are readily reconverted to monomers by mercaptoethanol, urea solutions or by extremes in pH.) Jones also treated serum albumin with N,N'-p-phenylene-bis-maleimide which react at the sulfhydryl group and form disulfide dimers but the thus treated composition was not found to significantly improve the potentiating capacity of albumin. Others have added polymeric materials such as dextran, polysucrose, polyvinylpyrrolidine, etc. but such modifications still are not sufficiently satisfactory. Thus, it is desirable to provide for a serological composition which has a higher and consistent potentiating capability, is stable in shipping and storage, and which may be manufactured without difficulty.

According to the present invention, there have been discovered new improved serological albumin compositions which have greater potentiating capabilities in antibody detection than the serum albumin compositions currently in use and which may be manufactured to provide compositions having consistent and reliable potentiating capabilities. The new improved serum albumin compositions comprise as essential ingredient, novel serum albumin polymer or polymers which in themselves constitute an aspect of the present invention. The expression "albumin" as herein employed whether in reference to a monomer or polymer is intended to refer to mammalian serum albumin. The novel polymer components of the serum albumin compositions are covalently bonded polymers in which each monomeric unit is joined to another by a peptide or amide bond, —NHCO—. The peptide bond is formed between an amino group of one albumin molecule and a carboxyl group of another albumin molecule and when formed becomes indistinguishable from other peptide bonds already existing in the molecule. The polymers contemplated for use in the novel serum albumin compositions may contain up to about 15 albumin units or higher but generally contain from about two to about eight monomeric units. The position of the amino group and the carboxyl group in the albumin molecules which participate in the peptide bond formation are not limited. Thus, both cross-linkages and linear-linkages are believed to exist. Dimers and trimers, and linearly joined higher polymers may be represented by the formula:

$$\text{H}_2\text{N}-\text{Alb}+\text{CONH}-\text{Alb}+{}_n\text{CONH}-\text{Alb}-\text{COOH} \qquad (I)$$

wherein $n$ is an integer (0 and 1 for dimer and trimer, respectively and greater than 1 for higher polymers). "Alb" as employed in the foregoing and subsequent formulas is a residue of a serum albumin molecule which may be represented by:

$$\text{H}_2\text{N}-\text{Alb}-\text{COOH} \qquad (II)$$

The novel serum albumin compositions of the present invention have far superior potentiating capabilities than existing compositions in the agglutination reactions of the IgG class of immune globulins. The compositions thus provide a highly sensitive antibody detecting medium by which it is possible to detect the presence of antibodies not heretofore possible with presently available agglutination potentiating compositions. They are also useful as diluents in the preparation of improved antisera compositions for use as blood grouping and blood typing reagents and as diluent medium for the suspension of red cells in serum/albumin and/or albumin/albumin titration for antibody detection.

The improved serological albumin compositions of the present invention comprise an albumin polymer as above set forth in admixture with a physiological or isotonic solution. A single polymer, a mixture of polymers, or a blend of monomer and polymer or polymers may constitute the albumin component of the compositions of the present invention. Good serological reactions are obtained employing as the albumin component, a blend of monomer and polymers which are obtained on the polymerization of monomeric albumin. Compositions containing a blend of monomers and polymers as obtained on polymerization may be referred to as a "polymerized albumin" solution. Serological compositions containing such blends in physiological solution constitute preferred embodiments of the present invention.

Generally, the total albumin content of the composition suitable for diagnostic purposes is from about 10 percent to about 35 percent by weight. Preferred compositions contain from about 16 percent to about 26 percent total albumin. By "total albumin" is meant the weight percent of albumin without regard to the monomeric or polymeric nature. The carrier for the albumin is physiological saline or isotonic solution as understood in the art.

In the preferred embodiment which contemplates a mixture of monomer and polymers, the novel polymers or a mixture of polymers is present in an amount of at least about 20 percent by weight of the total albumin content of the composition. Superior compositions may contain from about 46 percent to about 70 percent polymer, although highly desirable compositions may contain from about 28 percent to about 45 percent polymer. An example of the latter is a blend in which the approximate weight ranges of the monomer and polymer are as follows: Monomer 55-72% Dimer 15-23%, Trimer 5-8%, Tetramer 1-4%, Pentamer and Higher 5-15%. Generally, the weight ratio of monomer to polymer is from about 7:3 to about 1:9. Although polymers may be prepared in which a substantial portion of the polymer is higher than an octamer, highly desirable serological compositions are obtained when a substantial portion of the polymers are trimers and tetramers.

The serological albumin compositions of the present invention are clear, colored solutions of pH in the range of from about 6.5 to 8.0. The viscosity, dielectric constant and other properties vary depending on whether a single polymer, a mixture of polymers or a blend of monomer and polymers make up the albumin component, as well as the nature of the particular polymers. Generally, the relative viscosity (water as standard) is greater than about 2 and not more than about 25; the conductivity of solutions diluted 1:10 in distilled water at 0° C ranges from about $5 \times 10^{-4}$ mhos/cm$^2$ to about $7 \times 10^{-4}$ mhos/cm$^2$.

The polymers are true polymers in which the albumin monomer units are joined to each other in a covalent peptide or amide linkage or bond and are to be distinguished from aggregates of albumin which are frequently formed on treatment of albumin with cold alcohol or an aging and which are revertible to independent monomeric units. In the literature both the expression "polymers" and "aggregates" are found when reference is made to macromolecules formed on treating albumin with cold alcohol or an aging and which, on physical determinations such as electrophoretic mobility, exhibit apparent molecular weights which are multiples of the original albumin. However, the aggregates are formed by secondary bonding such as by hydrogen bonding and their formation is reversible and readily identified by techniques described in the literature. (Dunker et al., J. Biol. Chem. 224, 5074 (1969); Fairbanks et al., Biochem 10, 2606 (1971)). In such techniques, treatment of albumin solution with 2-mercaptoethanol converts noncovalently bonded "polymers" or aggregates to monomers. Electrophoresis of the sodium dodecyl sulfate complexes of the mercaptoethanol treated solution on a polyacrylamide column establishes the monomeric or polymeric nature of the compounds. Additionally, this technique (SDS-Polyacrylamide Gel Electrophoresis) may be employed to estimate the molecular weights of the various components. This is accomplished by plotting the mobility $$\text{mobility} = \frac{\text{distance of protein migration}}{\text{length of gel after staining}} \times \frac{\text{gel length before staining}}{\text{distance of dye migration}}$$

of known proteins against their molecular weight and then estimating the molecular weight of the experimental polymers by extrapolation from this curve. The polymerized albumin solutions of the present invention obtained as subsequently described have been shown by the foregoing technique to contain true polymers not revertible to monomers by 2-mercaptoethanol, urea, etc. The polymers of the present invention show properties appropriate for the particular polymer.

The polymers of the present invention are also to be distinguished from dimers which may be formed by treating albumin with a reagent such as N,N'-p-phenylene-bis-malemide which react at the sulfhydryl group of the albumin.

The improved serological serum albumin compositions containing the novel polymers may be prepared by first polymerizing serum albumin with a peptide bond forming reagent to obtain a polymer or mixture of polymers, and recovering polymer containing component either as a single polymer, a mixture of polymers, or preferably a blend of mixed polymers together with monomer, and employing said polymer containing component to produce the desired serological compositions by dissolving it in a physiological solution. When the improved serological compositions contains a mixture of polymers together with unpolymerized albumin, useful compositions may be obtained easily by polymerizing albumin as hereinafter described, quenching the reaction at the desired degree of polymerization, fractionating the reaction mixture to precipitate the albumin monomer-polymer mixture and reconstituting to a physiological solution as hereinafter more fully described.

The polymerization and the preparation of the novel polymers may be carried out by intimately contacting serum albumin with a peptide bond forming reagent whereupon a reaction takes place between an albumin molecule and the reagent with the formation of an intermediate followed by the reaction of the intermediate with another molecule of albumin to form a dimer of albumin which thereafter undergoes further similar reaction to form successively, a trimer, tetramer and higher polymers of albumin. The initial reactions to form the dimer (n in Formula I is 0) may be represented as follows (where "Reagent" refers to a peptide bond forming reagent):

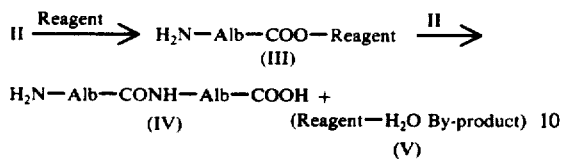

The dimer (IV) then may react with a molecule of reagent to form an intermediate $$H_2N-Alb-CONH-Alb-COO-Reagent \quad (VI)$$

which then reacts with another molecule of albumin to form a trimer (n in Formula I is 1) and the process repeated for higher polymers. In addition to the polymers, a by-product derived from the reagent is formed in each step, the exact nature of which depends on the reagent; however, the by-product will have incorporated into its structure, the elements of water.

Two groups of reagents which have been formerly employed in amide synthesis are especially useful for the preparation of polymerized albumin. These amide forming reagents are: (1) the 3-H isoxazolium salts reported by Woodward et al in J. Am. Chem. Soc. 83, 1010 (1961), and (2) the carbodiimides reported by Sheehan et al in J. Am. Chem. Soc., 77, 1067 (1955), U.S. 2,938,892 and 3,098,693. Other peptide link-forming reagents may be employed. Although not limited thereto, the preferred members of the peptide bond forming reagents may be selected from those described below and which may be prepared by methods described in the foregoing references. While other peptide forming reagents and/or means may be employed to obtain the polymers of the present invention, the foregoing reagents are especially useful for the preparation of serological compositions.

When the peptide bond forming reagent is a 3-H isoxozolium salt, the cation may be represented by the structure:

wherein $Q_1$ is preferably an aromatic radical such as phenyl or substituted phenyl, $Q_2$ is hydrogen or lower alkyl and $Q_3$ is lower alkyl. By "3-H-isoxazolium" is meant that at the 3-position, the substituent is hydrogen. The anion may be an independent ion or may be an internal anionic group. Representative of independent anions are fluoroborate, sulfonate, lower-alkyl phosphonate, methosulfate, ethosulfate, etc. When the anion is an internal anionic group, it may be supplied by a sulfonate substituted phenyl at $Q_1$. By "lower alkyl" as above employed is meant an alkyl radical containing from 1 to about 6 carbon atoms such as methyl, ethyl, n-propyl, isopropyl, n-butyl, amyl, hexyl, etc. Representative isoxazolium salts include N-ethyl-5-phenylisoxazolium-3'-sulfonate, N-methyl-5-phenylisoxazolium-3'sulfonate, N-ethyl-5-phenylisoxazolium fluoroborate, N-methyl-5-phenylisoxazolium fluoroborate, N-(n-propyl)-5-phenylisoxazolium-3'-sulfonate, N-(n-propyl)-5-phenylisoxazolium fluoroborate, etc.

In the reaction employing a 3-H-isoxazolium salt as the peptide bond forming reagent, the "Reagent" portion in the intermediates as exemplified in Formulas III and VI is the following group:

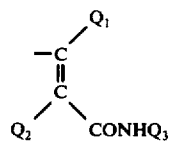

Thus, the intermediate of Formula III may be represented as:

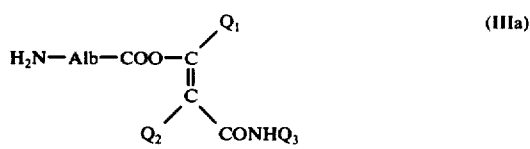

The by-product formed is a β-aroylamide which may be represented by the formula:

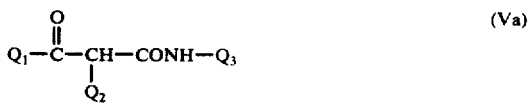

When the peptide bond forming reagent is a carbodiimide, it may be represented by the formula:

In this and succeeding formulas, at least one of R and R' is a radical in which the carbon atom attached to the nitrogen is an aliphatic carbon atom. Suitable radicals for R and R' include alkyl from about 2 to 12, preferably 2 to 6 carbon atoms, cyclohexyl, benzyl, phenethyl, lower alkylmorpholinyl, dilower alkylaminoalkyl, hydroxy-lower alkyl, lower alkyl piperidyl, phenyl, morpholino; and acid addition salts and quaternary ammonium salts. The carbodiimides most preferred are water-soluble. Carbodiimides bearing tertiary amino groups may be rendered water-soluble by forming an acid addition salt with mineral acids such as hydrohalic acids, sulfuric acid, nitric acid, phosphoric acid and with lower alkyl sulfonic and phosphonic acids; they may also be made water-soluble by quaternizing with a suitable quaternizing agent such as lower alkyl tosylates, halides and sulfates, e.g., methyl tosylate, methyl bromide, methyl iodide, ethyl tosylate, methyl sulfate, ethyl sulfate, benzyl bromide and the like.

Representative preferred reagents include: 1-ethyl-3-(3-dimethyl-aminopropyl)-carbodiimide hydrochloride, 1-cyclohexyl-3-(2-morpholinoethyl)-carbodiimide metho-p-toluene-sulfonate, 1-cyclohexyl-3-(4-diethylaminocyclohexyl)carbodiimide metho-p-toluene-sulfonate, 1-cyclohexyl-3-(β-diethylamino-ethyl)-carbodiimide, 1-ethyl-3-(2-morpholinoethyl)-carbodiimide hydrochloride, 1-ethyl-3-(2-morpholinoethyl)-carbodiimide sulfate.

In the reaction employing a carbodiimide as a peptide bond forming reagent, the "Reagent" portion in the intermediates as exemplified in Formulas III and VI and is the following group:

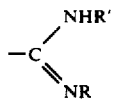

Thus, the intermediate of Formula III may be represented as:

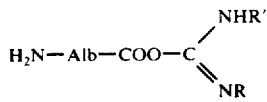 (IIIb)

The by-product formed in the reaction is a urea which may be represented by the formula:

 (Vb)

The polymerization may be carried out by intimately contacting an aqueous albumin solution, preferably a dilute aqueous solution, with a peptide bond forming reagent at a pH of from about 4.5 to about 6.0 at a temperature between about 2° C and about 60° C whereupon a reaction takes place with the formation of polymerized albumin, gererally a mixture containing polymeric products. When the desired extent of polymer formation is obtained, a basic nitrogen compound is added at temperatures in the range of 0°–30° C to destroy the excess reagent and quench the polymerization reaction. The polymer products thus obtained may be recovered by conventional procedures and therefter be employed as a mixture, separated to obtain individual polymers, or may be treated as subsequently described to obtain the serological albumin composition of the present invention.

For carrying out the polymerization step, the molar ratio of the peptide bond forming reagent to albumin may vary from about 1:1 to about 60:1 depending in part on whether the reagent is an isoxazolium salt or a carbodiimide. Thus, the ratio of reagent to albumin in the case of an isoxazolium salt is preferably from about 30:1 to about 60:1, while the ratio in the case of a carbodiimide is preferably from about 1:1 to about 30:1.

The exact concentration of albumin in the aqueous albumin solution starting material is not critical and may range from about 1.5 percent to about 20 percent. It is preferably a dilute solution in the range of from about 1.5 percent to about 4 percent. The peptide bond forming reagent is preferably employed in an aqueous solution. The exact concentration is not critical and generally only a sufficiency of water is employed to put the reagent in solution.

The serum albumin solution employed in the polymerization may be prepared from crystalline albumin; however, it is more conveniently prepared from higher concentration albumin solutions obtainable from manufacturing processes or sold commercially. Although not limited thereto, the serum albumin is generally bovine serum albumin because of the ready availability of beef blood.

In a preferred method for carrying out the polymerization, a concentrated aqueous solution of a peptide bond forming reagent is added with stirring while the temperature is maintained in the range of from about 2° C to about 40° C, to a dilute albumin solution which has previously been adjusted to a pH of from about 5.2 to about 5.6 with a dilute mineral acid e.g. hydrochloric, sulfuric, phosphoric acid, etc. The mixture is stirred after the addition for such time as necessary to obtain the desired amount of polymer formation. The extent of polymer formation may be determined by sampling the reaction mixture and subjecting the sample to polyacrylamide electrophoresis.

The polyacrylamide disc electrophoresis analysis method (Davis, B.J., Annals N.Y. Acad. Sci. 121, 404 (1964)) takes advantage of the fact that the pore size of the gels approach the molecular dimensions of the proteins and separation may be achieved through dimensional as well as charge differences. In this method of separation and analysis, samples are electrophoretically separated in polyarcylamide gel columns which are vertically placed between electrode holding upper and lower buffer reservoirs. The gel columns have an upper portion where electrophoretic concentration of sample ions takes place and a lower portion where the separation occurs. After electrophoretic separation, protein components which are detectable as separate discs on appropriate staining, may be determined quantitatively.

When the desired amount of polymerization has been achieved, the polymers may be recovered and/or separated by conventional procedures. However, when it is desired to employ the polymerized albumin in serological compositions for diagnostic purposes, the reaction is quenched with a basic nitrogen compound. The quenching step is essential if the ultimate compositions are to be employed for antibody detection, since compositions prepared omitting the quenching step are found to promote non-specific agglutination, thus, impairing its usefulness for specific antibody detection.

Suitable basic nitrogen compounds for the quenching step include glycine and other amino acids derivatives such as alanine, valine, isoleucine, ε-aminocaproamide, etc, or ammonium chloride. Although other basic nitrogen components such as alkylamines, e.g., ethylamine, propylamine, etc., aromatic or heterocyclic amines, may be employed to quench the reaction, it is desirable in the preparation of polymers to be employed in serological reactions to avoid the introduction of extraneous groups or structures. Generally, the amount of the basic nitrogen compound is added in an amount about equivalent to the amount of peptide bond forming reagent which initially had been added. In this way, not only the quenching of the polymerization but the destruction of excess reagent is assured.

The albumin polymers and monomer may be recovered from the polymerized and quenched reaction mixture by precipitating and removing the albumins therefrom. The albumins may be separated into components, if desired, and then may be dissolved in water or in physiological saline.

The serological albumin compositions of the present invention suitable as diagnostic agents may be prepared by precipitating the albumins, separating them from the reaction mixture and dissolving in a physiological solution. The operation is generally carried out by first adjusting the pH of the polymerized albumin reaction mixture to within the range of from about 4.5 to about 7.0 with mineral acid, and then while maintaining the temperature in the range of from about 0° C to about −20° C, adding alcohol whereupon the desired polymerized albumin product comprising a mixture of polymers together with some unpolymerized albumin precipitates. The precipitation is found to start when the alcohol concentration is about 25 percent and is substantially complete at about 40 percent. Suitable alcohols for carrying out the precipitation include methanol, ethanol, isopropanol and other water-miscible alcohols. The preferred method contemplates adding at a pH of about 5.0, sufficient alcohol to convert the reaction mixture to about a 40 percent alcoholic solution while the temperature is maintained in the range of from about −5° C to about −10° C. The precipitate is separated and recovered from the reaction mixture by conventional procedures, preferably centrifugation, and may be dissolved in aqueous saline to a 10 to 35 percent isotonic solution. The resulting serological albumin composition is a clear colored solution having the properties previously described.

Alternatively, the precipitate may be separated into single components by conventional procedures such as gel filtration method. When a serological albumin composition is to be prepared containing a single polymer, a 1 to 20 percent aqueous albumin mixture may be passed through a SEPHADEX G-200 (crosslinked dextran, Pharmacia Co., Uppsala, Sweden) column, and the polymers separated. The desired polymers may then be recovered by dissolving in physiological saline and concentrated to a 20-30 percent isotonic solution by ultrafiltration for analysis and serological testing.

The compositions thus obtained are suitable for use in various serological applications where non-polymerized albumin solutions previously have been employed by providing diagnostic media of far greater sensitivity and detection capabilities than heretofore thought possible. The compositions are not only unusually sensitive at high dilutions of test media but are found to reduce the prozoning phenomenon. The occurence of prozoning, i.e., failure of antibody of high agglutinin titer to agglutinate antigen, is obviously undesirable and provisions of detection media which reduces its occurrence is highly beneficial. Thus, the compositions are useful as potentiating agent in clinically significant antibody systems. In addition to its usefulness as potentiating media and antibody detection media, the compositions are useful wherever serum or red cell diluent is desired. Furthermore, these compositions are stable on shipping and storage.

The foregoing compositions may be utilized in specific diagnostic test utilizing immunological principles.

Thus, the composition may be employed to enhance antibody detection by red blood cells in hemagglutination reactions. In a representative typical operation, 2% suspensions of red cells containing antigen are prepared in the polymer containing albumin compositions of the present invention and employed to titrate test sera by adding one drop of the red cell suspension to a test tube containing two drops of the test serum or a suitable dilution thereof, incubating the mixture for 1 hour in a water bath maintained at 37° C, centrifuging at (usually 1000 rpm for one minute) and then examining for agglutination.

The composition may also be employed to detect antibody sensitized erthrocytes. In a representative typical operation, two drops of the polymer containing albumin composition is mixed together with a drop of a 4-6% red cell suspension previously sensitized with antibodies. The mixture is centrifuged and thereafter examined for extent of agglutination.

The following examples illustrate the invention but are not to be construed as limiting.

EXAMPLE I

Fourteen milliliters of 0.1 N hydrochloric acid is added to 500 milliliters of a 2% aqueous bovine albumin solution (of albumin content equal to or greater than 98% and consisting of 90% monomer and 10% dimeric aggregate). The pH after the addition is 5.4 To the resulting solution is added with stirring at ambient temperature, 5 milliliters of a 0.588 M 1-ethyl-3-(3-dimethylaminopropyl)carbodiimide hydrochloride solution (ratio of carbodiimide to albumin, 20:1) and the stirring continued for about 60 minutes to obtain polymerized bovine serum albumin product in the reaction mixture. At this time, 5 milliliters of 0.588 M glycine is added with stirring to the reaction mixture at ambient temperature and the stirring contained for about 15 minutes to quench the polymerization. Fifty milliliters of 0.1 N HCl is added to adjust the pH to about 5.0. Thereafter, 382 milliliters of methanol (previously cooled to 0° C) is added with stirring over a period of about 30 minutes to the reaction mixture while the temperature is maintained between about −2° C and −5° C, and the stirring continued for about 15 minutes after completion of the addition, whereupon the polymerized albumin product precipitates. The precipitate is recovered by centrifugation at 9000 r.p.m. for 30 minutes in a Model RC 2 Sorvall centrifuge and amounts to 20.4 grams of polymerized bovine serum albumin. The latter is reconstituted with a minimum volume of distilled water to obtain a 30.3% solution of polymerized bovine serum albumin.

A 0.7 milliliter portion of the 30.3% polymerized bovine serum albumin solution is admixed with 0.3 milliliter of a 0.9% sodium chloride solution to obtain a 22% polymerized serological bovine albumin solution. Polyacrylamide disc electrophoresis analysis (7% gel at pH 7.2) of this solution shows the following concentrations of monomers and polymers in percent by weight: 71% monomer, 21.2% dimer, 4.8% trimer, 1.1% tetramer and 1.9% higher polymers.

Serum albumin titration of $Rh_o$ positive cells with anti $Rh_o$ serum in the presence of 22% polymerized serological bovine albumin shows agglutination at 1/2048 dilution of anti $Rh_o$ serum.

EXAMPLE II

In a manner similar to that described in Example I, three milliliters of 1.0 N HCl is added at ambient temperature to 250 milliliters of 16.9% aqueous bovine serum albumin solution to adjust the pH of the solution to 5.4. Then, 20 milliliters of 0.248 M 1-ethyl-3-(3-dimethylaminopropyl) carbodiimide hydrochloride solution (ratio of carbodiimide to albumin, 8:1) is added with stirring and the stirring continued for 60 minutes to obtain a polymerized bovine serum albumin product. Twenty milliliters of 0.248 M glycine is then added to quench the polymerization. Thereafter, 5 milliliters of 1.0 N HCl is added to adjust the pH to 5.0, the mixture cooled, and, 197 milliliters of pre-cooled methanol added while the temperature is maintained between −2° C and −5° C whereupon polymerized bovine serum albumin product precipitates. The latter is recovered in a manner similar to that previously described and dissolved in distilled water to obtain 96 milliliter of 24.1% polymerized bovine serum albumin solution of pH 7.5. Polyacrylamide analysis of a sample of the solution shown the composition to be as follows: 32.6% monomer, 18.6% dimer, 12.6% trimer, 9.7% tetramer and 26.5% higher polymers.

A 22% serological polymerized albumin solution, prepared by admixing the foregoing with sodium chloride solution in a manner similar to that described in Example I, is employed to conduct serum albumin titration of $Rh_o$ positive cells with anti $Rh_o$ serum in its presence. Agglutination is obtained at a dilution of anti $Rh_o$ serum greater than 1/2048 whereas maxium dilution for agglutination in the presence of 22% non-polymerized albumin control is 1/512.

EXAMPLE III

In a similar manner. 0.1 N HCl is added to 10 milliliters of an 1.5% aqueous bovine serum albumin solution to adjust the pH from 5.6 to 5.4. To the resulting solution is added 0.6 milliliter of a 0.23 M N-ethyl-5-phenylisoxazolium-3'-sulfonate (ratio of isoxazolium sulfonate to albumin, 60:1) and the resulting mixture stirred at ambient temperature for about 60 minutes to obtain a polymerized bovine serum albumin product. Then an amount of glycine equivalent to the isoxazolium sulfonate is added and stirred to quench the reaction. This polymerized albumin mixture is then subjected to polyacrylamide gel electrophoresis showing a composition of: 77% monomer, 15.5% dimer, 5.2% trimer and 1.8% tetramer ahd higher polymers.

EXAMPLE IV

This example illustrates polymerized bovine albumin compositions of varying monomer and polymer contents and (1) inhibition of prozoning and (2) enhanced antibody detection capability of antigen bearing red cells at high dilutions of serum by employing polymerized serological albumin compositions as potentiating agent in hemagglutination reactions.

Polymerized bovine serum albumin composition are prepared in the manner similar to that described in Example I. These compositions have monomer and polymer contents as set forth in Table I.

TABLE I

| Albumin Composition | Monomer-Polymer Content in Percent by Weight | | | | |
|---|---|---|---|---|---|
| | Monomer | Dimer | Trimer | Tetramer | Higher |
| A | 67.9 | 21.3 | 7.2 | 3.6 | — |
| B | 59.5 | 21.1 | 7.0 | 2.4 | 10.0 |
| C | 70.5 | 21.6 | 5.9 | 2.0 | — |
| D | 62.8 | 18.5 | 6.0 | 2.8 | 9.9 |
| E | 67.3 | 20.1 | 5.1 | 1.5 | 6.0 |

Serological compositions of 22% total albumin having the foregoing monomer and polymer content are prepared in physiological saline as previously discussed. The compositions are employed in serum albumin titrations of Anti-D (anti-$Rh_o$). For such titrations, 2% suspensions of red cells containing D(+) antigen are prepared in the several 22% polymerized bovine serum albumins solutions of the above monomer-polymer content. As controls, 2% suspensions of red cells containing D(+) antigen are prepared in 22% unpolymerized bovine serum albumin corresponding to the albumin employed in the preparation of the polymerized compositions. The foregoing antigen containing compositions are employed to titrate previously prepared dilutions of anti-D serum in normal AB serum. The titrations are carried out by placing two drops of serum in a test tube and adding one drop of the D(+) antigen containing composition, incubating the mixture for one hour in a water bath maintained at 37° C, thereafter, centrifuging at 1000 r.p.m. for 1 minute and then examining for agglutination. The results at low dilutions showing inhibition of prozoning when polymerized serum albumin compositions are employed in titrations are seen in Table II.

TABLE II

| Albumin Reagent from | Reactivity[1] at Low Dilution | | |
|---|---|---|---|
| | Reciprocal of Anti-D Dilution | | |
| | 1 | 2 | 4 |
| Composition A | + | + | + |
| Control | * | * | + |
| Composition B | + | + | + |
| Control | 0 | 0 | 0 |
| Composition C | + | + | + |
| Control | 0 | * | + |
| Composition D | + | + | + |
| Control | 0 | 0 | * |
| Composition E | + | + | + |
| Control | 0 | 0 | * |

[1] + indicates agglutination (from 3 to 7 on a scale of 7); *indicates weak agglutination (from <1 to 2); 0 indicates no agglutination.

The results showing enhanced detection at high dilutions when polymerized serum albumin compositions are employed in titrations are seen in Table III.

TABLE III

| Albumin Reagent from | Reactivity[1] at High Dilution | |
|---|---|---|
| | Reciprocal of Anti-D Dilution | |
| | 1024 | 2048 |
| Composition A | * | 0 |
| Control | 0 | 0 |
| Composition B | * | * |
| Control | 0 | 0 |
| Composition C | * | 0 |
| Control | 0 | 0 |
| Composition D | + | 0 |
| Control | 0 | 0 |
| Composition E | + | + |
| Control | 0 | 0 |

[1]Same notation as Table II.

EXAMPLE V

This sample illustrates the enhanced ability to detect antibody sensitized erythrocytes by employing polymerized serological albumin compositions in hemagglutination reactions.

For such determination, polymerized albumin solutions having the monomer to polymer distribution of Compositions C, D and E in Example IV, are employed to prepare compositions in physiological saline in which the albumin concentration varies from 20% to 30% by weight. As controls two separate unpolymerized bovine serum albumin solutions (unpolymerized No. 1 and No. 2) are prepared also in the same concentration range. For the determination of the potentiating effect, 2 drops of the albumin solutions and 1 drop of Coombs Control reagent (red cells coated with antibody globulin) are mixed together and centrifuged for 15 seconds at 3400 r.p.m. and thereafter observed for extent of agglutination. The results are seen in the following table:

TABLE IV

| Albumin Reagent from | Reactivity[1] with Anti-D Sensitized Red Blood Cells | | | | | |
|---|---|---|---|---|---|---|
| | Total Albumin Concentration (%) | | | | | |
| | 30 | 28 | 26 | 24 | 22 | 20 |
| Composition C | + | + | + | + | + | * |
| Composition D | + | + | + | + | * | * |
| Composition E | + | + | + | * | * | * |
| Unpolymerized #1 | * | * | 0 | 0 | 0 | 0 |
| Unpolymerized | | | | | | |

TABLE IV-continued

| Albumin Reagent from | Reactivity[1] with Anti-D Sensitized Red Blood Cells | | | | | |
|---|---|---|---|---|---|---|
| | Total Albumin Concentration (%) | | | | | |
| | 30 | 28 | 26 | 24 | 22 | 20 |
| #2 | 0 | 0 | 0 | 0 | 0 | 0 |

[1]Same notation as Table II

EXAMPLE VI

Separation of polymerized bovine albumin composition having a monomer-polymer distribution of Composition D in Example IV into its components are carried out in the following manner.

4.5 milliliters of a 26.6% polymerized albumin composition is mixed with 10.5 milliliters of buffer (0.1 M trishydroxymethylaminomethane hydrochloride with 1.0 M sodium chloride and Trimerosal (1:10,000)) at pH 8.0. Ten milliliters of this mixture is put on a column (2.5 × 93 cm = 456 ml) of SEPHADEX G-200 (cross-linked dextran, Pharmacia Co.). This mixture is eluted with a mixture of 0.1 M trishydroxymethylaminomethane hydrochloride and 1.0 M sodium chloride at pH 8 with a flow rate of 18 milliliters per hour at 5° C to recover each of the component monomer and polymers.

The molecular weight of the components are determined by employing the SDS-Polyacrylamide gel electrophoresis technique to determine mobility and then plotting the mobility on a curve employing known polymers, with published molecular weights as standard. The results shown in Table V are obtained:

TABLE V

| Albumin Component | Mobility | Molecular* Weight |
|---|---|---|
| Monomer | 0.598 | 68,000 |
| Dimer | 0.321 | 150,000 |
| Trimer | 0.205 | 220,000 |
| Tetramer | 0.145 | 250,000 |
| Pentamer | 0.026 | 365,000 |

*Based on curve employing following standards: Ovalbumin monomer, mobility 0.727, m.w. 43,000; Transferrin (human), mobility 0.468, m.w. 90,000; Bovine serum albumin monomer (twice crystallized), mobility 0.564, m.w. 69,000.

EXAMPLE VII

This example illustrates the enchanced antibody detection capability of albumin compositions prepared from various albumin polymer components obtained by fractionation of a polymerized mixture in the manner described in Example VI. The operations are carried out at 10% total albumin content, far below preferred concentrations and illustrates the enchanced potentiation capability of polymer components.

Serological compositions of 10% albumin in isotonic solution are prepared from each of the components as well as from unfractionated polymerized and nonpolymerized albumin solutions as controls. Red cells containing D(+) antigen are added to each of the albumin solutions to obtain compositions containing 2% suspension of red cells. The compositions are employed in serum albumin titrations carried out in a manner similar to that described in Example IV to determine their potentiation effect on anti $Rh_o$-$Rh_o$ (anti-D-D) agglutination.

Agglutinations are observed for dilutions as high as 1/32 when the albumin component is a dimer or a trimer and for dilutions as high as 1/512 when the albumin component is tetramer plus higher polymers. Agglutinations are observed at dilutions of 1/128 when the albumin is an unfractionated polymerized mixture.

When the albumin is a monomer obtained by fractionation of a polymerized mixture or an unpolymerized albumin, no agglutination is observed even when the anti-D serum is undiluted.

EXAMPLE VIII

In an operation similar to that described in Examples I and II, 0.248 M aqueous solution of 1-cyclohexyl-3-(2-morpholinoethyl)carbodiimide metho-p-toluene sulfonate is added with stirring to 2500 milliliters of a solution of 16.9 percent aqueous bovine serum albumin, previously adjusted to a pH of about 5.4. After completion of the addition the stirring is continued for about two hours to obtain polymerized bovine albumin. Two hundred milliliters of glycine is then added to quench the polymerization, the pH then adjusted to 5.0 with dilute hydrochloric acid and the mixture cooled. Thereafter, precooled methanol is added to precipitate the polymerized albumin mixture. The solids are separated by ultracentrifugation, and dissolved in physiological saline. The resulting composition may be usefully employed as a potentiating agent in hemagglumation reactions.

EXAMPLE IX

In polymerization reactions carried out in operations similar to that described in Examples I, II and III, the following polymerized compositions may be prepared:

A polymerized albumin mixture containing about 25 percent by weight of monomeric and about 75 percent by weight of a mixture substantially of dimer, trimer, tetramer, pentamer, hexamer, heptamer and octamer by the reaction of aqueous 12 percent bovine serum albumin and 1-cyclohexyl-3-(4-diethylaminocyclohexyl)-carbodiimide metho-p-toluene sulfonate.

A polymerized albumin mixture containing about 17 percent by weight of monomer and about 83 percent by weight of a mixture of polymers of from 2 to about 15 alubumin units by the reaction of aqueous 10 percent bovine serum albumin and 1-cyclohexyl-3($\beta$-diethylaminoethyl)-carbodiimide hydrochloride.

A polymerized albumin mixture containing about 10 percent by weight of monomer and about 90 percent by weight of a mixture of polymers of from 2 to about 8 albumin units by the reaction of aqueous 4 percent bovine serum albumin and 1-ethyl-3-(3-dimethyl-aminopropyl)carbodiimide hydrochloride.

A polymerized albumin mixture containing about 50 percent by weight of monomers and about 50 percent by weight of a mixture of polymers primarily of from 2 to about 6 albumin units by the reaction of aqueous 4 percent bovine serum albumin and N-propyl-5-phenylisoxazolium-3'-sulfonate.

A polymerized albumin mixture containing about 45 percent by weight of monomer and about 55 percent by weight of a mixture of polymers containing high proportion of trimers and tetramers by the reaction of aqueous 3 percent bovine serum albumin and N-ethyl-5-phenylisoxazolium fluoroborate.

In further operations carried out in a manner similar to that described in Examples I and II, the polymer mixtures may be treated with alcohol (after first adjusting the pH) to precipitate the albumins, the precipitated albumins separated and recovered, and then dissolved in physiological saline to produce serological compositions of 15, 25 and 35 percent total albumin content.

EXAMPLE X

Single polymers may be obtained from a polymerized bovine albumin solution in a manner similar to that described in Example VI. Each polymer is separately dispersed in physiological saline to produce diagnostic reagent compositions of 24 percent polymer. The compositions may be used for potentiating hemagglutination reactions.

What is claimed is:

1. A bovine serum albumin composition suitable for use in specific antibody detection and for antibody sensitized erythrocyte detection comprising at least one polymer of bovine serum albumin in an aqueous solution, said polymer or polymers being homopolymers in which from 2 to about 15 monomeric albumin units are joined to each other through a convalent peptide bond, said composition having a total albumin content of from about 10 percent to about 35 percent by weight of the composition; and wherein the albumin component of said aqueous composition is prepared by a method comprising (i) intimately contacting bovine serum albumin with a peptide bond forming reagent selected from the group consisting of 3-H-isoxazolium salts and carbodiimide reagents to form albumin polymers, (ii) adding basic nitrogen compound to the polymerization mixture containing said polymers to quench the reaction and to substantially destroy excess peptide bond forming reagent, (iii) acidifying the mixture to a pH of about 4.5 to 7, and (iv) thereafter recovering the albumin monomers and polymers.

2. The composition of claim 1 where, in the preparation of the albumen component, step (iii) comprises acidifying the mixture to a pH of about 5.

3. The composition of claim 1 in which the aqueous solution is a saline solution.

4. The composition of claim 1 which contains in addition, a serum albumin monomer, provided that at least 20 percent of the total albumin is polymer.

5. The composition of claim 4 wherein the polymer component of the albumin composition is from about 28 percent to about 45 percent of the total albumin.

6. The composition of claim 4 wherein the polymer component of the albumin composition is from about 46 percent to about 70 percent of the total albumin.

7. The composition of claim 4 wherein the aqueous solution is a saline solution, the polymers are those having from 2 to about 8 monomeric units and the monomer to polymer ratio is from about 7:3 to about 1:9.

8. The composition of claim 4 wherein the aqueous solution is a saline solution, the polymers are those having from 2 to about 8 monomeric units, and the monomer and polymers are present in the following amounts by weight of the total albumin: monomer, about 55-72 percent; dimer, about 15-23 percent; trimer, about 5-8 percent; tetramer, about 1-4 percent; and pentamer and higher about 5-15 percent.

9. A method for detecting anti-D antibody sensitized erythrocytes comprising
  1. intimately admixing with the anti-D antibody containing red cell suspension, a serological albumin composition comprising the composition of claim 3 and
  2. centrifuging the resulting mixture and observing for agglutination.

10. A method for detecting anti-D antibodies in hemagglutination reactions comprising
  1. preparing a titrating composition by intimately admixing an erythrocyte suspension containing D(+) antigen and a serological albumin composition comprising the composition of claim 3.
  2. intimately admixing said titrating composition with test serum, and
  3. incubating and centrifuging the resulting mixture, and thereafter observing for agglutination.

* * * * *